(12) United States Patent
Bertaux et al.

(10) Patent No.: US 6,719,837 B2
(45) Date of Patent: Apr. 13, 2004

(54) PEARLESCENT PIGMENTS

(75) Inventors: Stéphane Bertaux, Pfungstadt (DE);
Peter Reynders, Griesheim (DE);
Jens-Uwe Wichmann, Freiburg (DE);
Eberhard Schweda, Moessingen (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 0 days.

(21) Appl. No.: 10/355,024

(22) Filed: Jan. 31, 2003

(65) Prior Publication Data

US 2003/0147820 A1 Aug. 7, 2003

(30) Foreign Application Priority Data

Feb. 1, 2002 (EP) .............................. 02002448

(51) Int. Cl.$^7$ .............................. C04B 14/20
(52) U.S. Cl. ................ 106/415; 106/416; 106/417; 106/418; 106/419; 106/450; 106/455; 106/461; 106/479; 106/480; 106/481
(58) Field of Search ................ 106/415–417, 106/419, 425, 431, 435, 438, 441, 450, 455, 461, 479, 480, 481

(56) References Cited

U.S. PATENT DOCUMENTS 5,246,493 A     9/1993   Nagasaki et al.
5,540,770 A * 7/1996   Schmid et al. .............. 106/415

FOREIGN PATENT DOCUMENTS

EP     0 401 141 A1    12/1990
WO   WO 00/17277 A1    9/1999

OTHER PUBLICATIONS

Marchand et al., "Nitrides and Oxynitrides: Preparatoin, Crystal Chemistry and Properties," *Journal of the European Ceramic Society*, vol. 8, 1991, pp. 197–213.

* cited by examiner

Primary Examiner—C. Melissa Koslow
Assistant Examiner—Shalie Manlove
(74) Attorney, Agent, or Firm—Millen, White, Zelano & Branigan, P.C.

(57) ABSTRACT

The present invention relates to pearlescent pigments based on substrates coated with one or more layers of nitrides or oxynitrides to a method for the production of such pigments and their use in plastics, paints, coatings, powder coatings, inks, printing inks, glasses, ceramic products, agriculture foils, for lasermarking of papers and plastics, security applications and in cosmetic formulations.

19 Claims, No Drawings

PEARLESCENT PIGMENTS

The present invention relates to pearlescent pigments based on substrates coated with one or more layers of nitrides or oxynitrides, to methods for the production of such pigments and to their use in plastics, paints, coatings, powder coatings, inks, printing inks, glasses, ceramic products, agriculture foils, for lasermarking of papers and plastics and in cosmetic formulations.

The pearlescent pigments that are used and prepared according to this invention are at least partially transparent pigments with an angle-dependent optical effect.

Absorption pigments without any substrates based on nitrides or oxynitrides are well known. A good overview over these substances can be found in Marchand et al. "Nitrides and Oxynitrides: Preparation, Crystal Chemistry and Properties," *Journal of the European Ceramic Society*, 8 (1991), p 197–213. It is characteristic for these pigments that through the variation of the metal oxides or mixed oxides and/or a variation in the N/O ratio a wide range of the color spectrum can be covered. These pigments are synthesized by simply mixing the metal oxides together with a mineralizer and subsequently heating this mixture under an ammonia gas atmosphere.

Titanium nitride coated substrates used as conductive pigments and produced in a fluidized bed reactor are disclosed in EP-A 0 401 141. Here, substrate particles were to be made conductive by a coating with titanium nitride. To achieve this, mica powder is coated via CVD in a fluidized bed apparatus at a constant temperature. As reactants a titanium halide and ammonia, mixed with an inert gas such as argon, are used.

Titanium oxynitride coated $SiO_2$ platelets are disclosed in WO2000/17277. In this application $TiO_2/SiO_2$-flakes are reduced with a metal under a non-reductive atmosphere at high temperatures using a metal halide as accelerator. The resulting product consists of titanium oxynitride-coated $SiO_2$ platelets and titanium suboxide coated $SiO_2$ platelets. Titanium nitride and oxynitride layers made according to this technology have turned out to be non-continuous and consequently showing brownish to olive colors. These rather unattractive colors were already described in the examples of WO 2000/17277.

It was therefore an object of the present invention to provide pigments with a great variety of different masstones which combine an attractive angle dependant interference phenomenon with the absorption color, therewith extending the range of pearlescent pigments based on substrates coated with nitrides/oxynitrides. Upon further study of the specification and appended claims, further objects and advantages of this invention will become apparent to those skilled in the art.

The present invention now provides new kinds of pigments which are based on nitride, respectively, oxynitride layers on substrates. These pigments are based on substrates coated with a selectively absorbing layer.

Surprisingly, a pearlescent pigment has now been found, which is based on substrates coated with one or more layers, characterized in that at least one layer is selectively light absorbing and consists of a nitride and/or oxynitride with the proviso that layers of titanium nitride or titanium oxynitride are excluded.

Preferably the synthesis of the new pigments is divided into two steps. The first step is the synthesis of a precursor and the second a conversion process carried out in a furnace. The new pigments can be produced in conventional static ovens, belt kilns or rotary kilns. However, a better product with less agglomerates and faster reaction rates is obtained in fluidized bed reactors.

The precursor is preferably produced in an aqueous precipitation process such as described for example in U.S. Pat. Nos. 3,087,828, 3,087,829, DE-A 19 59 998, DE-A 20 09 566, DE-A 22 14 545, DE-A 22 44 298, DE-A 23 13 331, DE-A 25 22 572, DE-A 31 37 808, DE-A 31 37 809, DE-A 31 51 343, DE-A 31 51 354, DE-A 31 51 355, DE-A 32 11 602, DE-A 32 35 107, WO 93/08237 and EP-A 0 763 573. Halide, carbonate, oxalate, chloride, oxychloride or alcoholate solutions are used to precipitate oxides, respectively, mixed oxides onto substrates. The reaction parameters such as temperature, pH, agitation velocity and reactor geometry are optimized to yield a flat continuous layer of insoluble oxides and/or hydroxides on the substrates. The mixed oxides are coprecipitated onto the substrates following an analogous process. For example, solutions of the different metal salts are mixed and then slowly added in the reactor to coat the substrate.

A wide range of precursors can also be synthesized using dopant ions, such as silicon, vanadium, chromium, aluminum, cerium, neodymium, praseodymium, sulfur, selenium, cobalt, nickel, zinc and phosphate ions, coprecipitated into the oxide respectively hydroxide layers. The dopants can be used to create color effects (like rare earth, vanadium, or cobalt ions) as well as for the control of grain growth (like $SiO_2$ or aluminum oxide) during the subsequent reaction with the reaction gas, such as ammonia. Advantageously this process does not need mineralizers or other reactive gases.

In the second step the precursors obtained in the above first step are converted into nitrides/oxynitrides. The precursors to be converted are calcined, for example, in a conventional static oven, belt kiln or rotary kiln. However, a better product with less agglomerates and faster reaction rates is obtained in a fluidized bed reactor. This process can be performed batchwise or continuously. A suitable mixture of gases consists of at least one inert and one reaction gas. Examples of useful reaction gases are $N_2$, or $N_2/H_2$, but preferably ammonia. Further examples of converting to nitrides are shown in U.S. Pat. No. 5,246,493 and the above-cited Marchand article. Suitable inert gases are Ar, $H_2/CO/N_2$, $N_2$ (at lower reaction temperatures). The gas composition may vary from >0 to 100 vol.-%, preferably from 20 to 80 vol.-% of reaction gas in inert gas.

The temperature is maintained during calcinations, for example, at a fluidized bed temperature at 700 to 1250° C., preferably 800° C. to 1100° C. The conversion from oxides/ mixed oxides to nitrides/oxynitrides is carried out depending on the different parameters, such as gas flow rates, reaction time or temperature profiles. The longer the reaction time the higher the nitride-to-oxynitride ratio. Consequently the reaction time determines the obtained structure of the compound. The color and the color strength of compounds is associated to a specific structure; thus, it is preferred that the reaction time is well controlled. In addition, for the same reason, temperature control is desirable.

In order to maintain the almost ideal conditions prevalent in a homogeneous fluidized bed in comitercurrent/cocurrent contacting special devices may be used. Instabilities like formation of channels or of bubbles in the bed are instantly destroyed by vibrations or agitating facilities.

If the reaction with the reaction gas, preferably ammonia, is not carried out to full completeness, mixtures of phases can be obtained including gradient of phase concentration through the layer thickness. These incompletely reacted products can be advantageous with respect to a desired color shade.

Suitable substrates which can be used in the present invention as base material, include, for example, spherical or platelet-shaped substrates, especially preferred are natural micaceous iron oxide (for example as in WO 99/48634), synthetic and doped micaceous iron oxide (for example as in EP-A 0 068 311), mica (muscovite, phlogopite, fluorophlogopite, synthetic fluorophlogopite, talc, kaolin), basic lead carbonate, flaky barium sulfate, $SiO_2$, $Al_2O_3$, $TiO_2$, glass, ZnO, $ZrO_2$, $SnO_2$, BiOCl, chromium oxide, BN, MgO flakes, $Si_3N_4$, graphite, pearlescent pigments (including those which react under the fluidized bed conditions to nitrides, oxynitrides or by reduction to suboxides etc.) (for example EP-A 9 739 066, EP-A 0 948 571, WO 99/61529, EP-A 1 028 146, EP-A 0 763 573, U.S. Pat. No. 5,858,078, WO 98/53012, WO 97/43348, U.S. Pat. No. 6,165,260, DE-A 15 19 116, WO 97/46624, EP-A 0 509 352), pearlescent multilayer pigments (for example EP-A 0 948 572, EP-A 0 882 099, U.S. Pat. Nos. 5,958,125, 6,139,613), coated or uncoated $SiO_2$ spheres (for example known from EP-A 0 803 550, EP-A 1 063 265, JP-A 11 322 324), EP-A 0 803 550, EP-A 1 063 265, JP-A 11 322 324), micro bubbles (U.S. Pat. No. 4,985,380). Particularly preferred are mica, $SiO_2$ flakes, $Al_2O_3$ flakes, $TiO_2$ flakes, $Fe_2O_3$ flakes, BiOCl and glass flakes.

The layer(s) that is (are) precipitated onto the substrates and then converted result in the following nitrides and/or oxynitrides, for example:

in case of nitrides:
1) binary nitrides of the formula
-$A_xN_y$ with A=Ta, Zr, Si, Al, V, Nb, Cr, Mn, W, Mo, Fe, Li, Mg, Ca, Sr, Zn, Ga, P particularly $Ta_3N_5$, $Zr_3N_4$, $Si_3N_4$, $Fe_3N$, GaN, CrN
$0<x$, $0<y$ 2) ternary nitrides of the formula
$A_xB_yN_z$ such as $NaPN_2$, $NaGe_2N_3$, $MgSiN_2$, $BeSiN_2$, $MgSiN_2$, $MnSiN_2$, $MgGeN_2$, $MnGeN_2$, $ZnGeN_2$, $LiSi_2N_3$, $LiGe_2N_3$, $NaGe_2N_3$, $Mg_2PN_3$, $Mn_2PN_3$, $Zn_2PN_3$, $LaSi_3N_5$, CrYN, CrScN, CrLaN,
$0<x$, $0<y$, $0<z$ $Li_{2n-3}M_nN_{n-1}$ with the oxidation state n of the metal M ranging from 2 to 6, such as LiMgN, LiZnN, $Li_3AlN_2$, $Li_3GaN_2$, $Li_5SiN_3$, $Li_7VN_4$, $Li_7MnN_4$, $Li_9CrN_5$, $Li_2ZrN_2$, $Li_2CeN_2$, $Ca_2ZnN_2$, in case of oxynitrides:
1) oxynitrides based on one metal
$A_xO_yN_z$, with A=Ta, Al, Zr, Nb, Si, P, Hf, particularly $Zr_7O_8N_4$, $Zr_2ON_2$, $Zr_7O_{11}N_2$, $Hf_2ON_2$, $Al_3O_3N$, $Ga_{1-x/3}N_{1-x}O_x$ with $0<x<1$
$0<x$, $0<y$, $0<z$ 2) oxynitrides based on two metals
$ABO_2N$, with A=Lanthanide, B=Si, particularly: $LaSiO_2N$
$ABO_2N$, with A=Ca, Sr or Ba B=Ta or Nb particularly: $CaTaO_2N$, $SrTaO_2N$, $SrNbO_2N$, $BaTaO_2N$, $BaNbO_2N$
$ABON_2$, with A=Lanthanide, B=Ta, Nb, particularly: $LaTaON_2$
ABON, with A=alkaline and B=Ge or Si particularly: NaGeON, KGeON, LiSiON, NaSiON
$A_2BO_3N$, with A=Ca, Sr, Ba and B=Ta, Nb
$ABO_{3-x}N_x$, with A=$Li^+$, $Na^+$, $K^+$, $Rb^+$, $Cs^+$, $Ba^{2+}$, $Sr^{2+}$, $Pb^{2+}$, $Ln^{3+}$(=rare earth), $Bi^{3+}$, $Y^{3+}$ B=$W^{6+}Re^{6+}Mo^{5+}$, $Ta^{5+}$, $Nb^{5+}$, $Mo^{5+}$, $W^{5+}$, $Zr^{4+}$, $Sn^{4+}$, $Ge^{4+}$, $Nb^{4+}$, $Ta^{4+}$, $Al^{3+}$, $Ga^{3+}$, $Ln^{3+}$ (=rare earth), $Fe^{3+}$, $Cr^{3+}$ and with x=1, 2 or 3 and the electronic charges a of A and b of B verify a+b=6+x; a$\geq$x and solid solutions of these compounds
$ABO_3N$ with A=K or Cs B=Os particularly: $KOsO_3N$, $RbOsO_3N$, $CsOsO_3N$
$A_2BO_3N$ with A=Sr or lanthanide B=Ta particularly: $Sr_2TaO_3N$
$Li_{1+x}Ge_{2-x}O_{3x}N_{3-3x}$
(0<x<1)
$LnWO_xN_{3-x}$ with Ln=La and Nd and 0,6<x<0,8
$LnWO_3N$ with Ln=Nd, Sm, Gd, Dy
$Ln_{2.67}W_{1.33}O_{3.8}N_{2.8}$, $Ln_{14}W_4O_{33-3x}N_{2x}$, and $Ln_6W_4O_{12-3x}N_{2x}$ with 0<x with Ln=Ho, La, Nd, Sm, Y, Yb, and other alike defect compounds having a structure of $A_4X_{6.6}\Delta_{1.4}$ and $A_4X_{7.33\ to\ 6.85}\Delta_{0.67\ to\ 1.15}$, in which A=cations such as rare earth and tungsten, X=oxygen and nitrogen as anions, and $_\Delta$ is a defect.
$Ln_2AlO_3N$ with Ln=La, Nd, Sm
$Ln_{10}Si_6O_{24}N_2$ with Ln=La, Ce, Nd, Sm, Gd and Y
$Ln_2Si_3O_3N_4$ with Ln=La—Yb and Y
$Zr_{(x)}Ta_{(3-x)}O_{(x)}N_{(5-x)}$ with $0\leq x\leq 0.66$
$Ta_{(1-x)}Zr_{(x)}N_{(1-x)}O_{(1+x)}$ with $0\leq x\leq 0.28$ 3) oxynitrides based on three metals
$AZr_xTa_{1-x}O_{2+x}N_{1-x}$ with A=Ca, Sr, Ba, 0<x<1
LiNaPON, $Re_6WV_{2+x}O_{12-3x}N_{2x}$ with 0<x
$Ln_8Cr_2Si_6O_{24}N_2$ with Ln=La—Dy (i.e., an element between La and Dy, inclusive, in the Periodic Table)
$Ln_8M^{IV}_2Si_6N_4O_{22}$ with Ln=La—Dy and $M^{IV}$=Ti or Ge
$LnEu''SiO_3N$ with Ln=La, Nd, Sm
$Ln_4Si_2N_2O_7$ with Ln=Nd—Yb (i.e., an element between Nd and Yb, inclusive, in the Periodic Table) and Y Pyrochlore structure: $A_xA'_{2-x}B_2O_{5+x}N_{2-x}$ or $A'_2B_{2-y}B'_yO_{5+y}N_{2-y}$
A=$Mg^{2+}$, $Ca^{2+}$, $Sr^{2+}$, $Ba^{2+}$, $Zn^{2+}$
A'=$Ln^{3+}$ (=rare earth), $Bi^{3+}$, $Al^{3+}$, $Fe^{3+}$
B=$V^{5+}$, $Nb^{5+}$, $Ta^{5+}$, $Mo^{5+}$, $W^{5+}$
B'=$Zr^{4+}$, $Hf^{4+}$, $Sn^{4+}$, $Ge^{4+}$, $Si^{4+}$, $Nb^{4+}$, $Ta^{4+}$
$0\leq x$, y<2, with the exception $Ln_2TaO_5N_2$ Spinel structure: $CD_{2-m}D'_mO_{4-m}N_m$ or $C_{1-n}C'_nD_2O_{4-n}N_n$
C=$Mg^{2+}$, $Ca^{2+}$, $Mn^{2+}$, $Fe^{2+}$, $Co^{2+}$, $Ni^{2+}$, $Zn^{2+}$
D=$Al^{3+}$, $Ga^{3+}$, $In^{3+}$, $Ti^{3+}$, $V^{3+}$, $Cr^{3+}$, $Fe^{3+}$, $Co^{3+}$, $Ni^{3+}$
D'=$Zr^{4+}$, $Hf^{4+}$, $Sn^{4+}$, $Ge^{4+}$, $Si^{4+}$, $Nb^{4+}$, $Ta^{4+}$
C'=$Al^{3+}$, $Ga^{3+}$, $In^{3+}$, $Ti^{3+}$, $V^{3+}$, $Cr^{3+}$, $Fe^{3+}$, $Co^{3+}$, $Ni^{3+}$
0<m<2, $0<n\leq 1$ Elpasolite structure: $A'_2QBO_{5-z}$, $N_{1+z}$
z=0 Q=C (bivalent metallic ion) $A'_2CBO_5N$
z=1 Q=A" (trivalent metallic ion) $A'_2A''BO_4N_2$
z=2 Q=D" (tetravalent metallic ion) $A'_2D''BO_3N_3$
A', B, C and D are defined above and
A" represents $Ln^{3+}$ (=rare earth) or $Bi^{3+}$
D" denotes a tetravalent metal ion Perovskite structure: $A_{1-u}A'_uBO_{2-u}N_{1+u}$ or $A'B_{1-w}B'_wO_{1+w}N_{2-w}$
A=$Mg^{2+}$, $Ca^{2+}$, $Si^{2+}$, $Ba^{2+}$
A'=$Ln^{3+}$ (=rare earth), $Bi^{3+}$, $Al^{3+}$, $Fe^{3+}$
B=$V^{5+}$, $Nb^{5+}$, $Ta^{5+}$
B'=$Zr^{4+}$, $Hf^{4+}$, $Sn^{4+}$, $Ge^{4+}$
$0\leq u<1$; $0<w\leq 1$, with the exception $Ln_2TaON_2$ The thickness of the nitride respectively oxynitride layers can vary, for example, between 5 and 500 nm, yielding slight shades and flat angle color effect at low thicknesses and very pronounced hiding at high thicknesses. For the optimal interference effect, the preferred thicknesses are 50–350 nm, especially preferred 80–200 nm.

Preferred pearlescent pigments of the present invention are given in the following:

substrate+$Ta_xO_yN_z$, preferably TaON (x=y=z=1)
substrate+$Zr_xO_yN_z$, preferably $Zr_2ON_2$ or $Zr_7O_8N_4$
substrate+V doped $Zr_xO_yN_z$, preferably V-doped $Zr_2ON_2$ or $Zr_7O_8N_{4w}$ substrate+LaTaON$_2$
substrate+Pr doped Zr$_x$O$_y$N$_z$, preferably Pr-doped Zr$_2$ON$_2$ or Zr$_7$O$_8$N$_4$
substrate+CaTaO$_2$N
substrate+SrTaO$_2$N
substrate+Zr$_2$ON$_2$
substrate+Zr$_7$O$_8$N$_4$
substrate+Ta$_3$N$_5$
substrate+TaON
substrate+ZrV$_2$O$_4$N$_2$
substrate+ZrPr$_6$O$_{10}$N$_2$
substrate+TiON+Ta$_3$N$_5$
substrate+Ta$_3$N$_5$+TiO$_2$
substrate+TiO$_2$+SiO$_2$+Ta$_3$N$_5$
substrate+Zr$_2$ON$_2$+TiO$_2$
substrate+TiON+Zr$_2$ON$_2$
substrate+TiO$_2$+Zr$_2$ON$_2$ Especially preferred pigments are given in the following:

Mica+Ta$_x$O$_y$N$_z$
Mica+Zr$_x$O$_y$N$_z$
Mica+V doped Zr$_x$O$_y$N$_z$
Mica+LaTaON$_2$
Mica+Pr doped Zr$_x$O$_y$N$_z$
Mica+CaTaO$_2$N
Mica+SrTaO$_2$N
Mica+Zr$_2$ON$_2$
Mica+Zr$_7$O$_8$N$_4$
Mica+Ta$_3$N$_5$
Mica+TaON
Mica+ZrV$_2$O$_4$N$_2$
Mica+ZrPrO$_{10}$N$_2$
Mica+TiON+Ta$_3$N$_5$
Mica+Ta$_3$N$_5$+TiO$_2$
Mica+TiO$_2$+SiO$_2$+Ta$_3$N$_5$
Mica+Zr$_2$ON$_2$+TiO$_2$
Mica+TiON+Zr$_2$ON$_2$
Mica+TiO$_2$+Zr$_2$ON$_2$
SiO$_2$ flakes+Ta$_x$O$_y$N$_z$
SiO$_2$ flakes+Zr$_x$O$_y$N$_z$
SiO$_2$ flakes+V doped Zr$_x$O$_y$N$_z$
SiO$_2$ flakes+LaTaON$_z$
SiO$_2$ flakes+Pr doped Zr$_x$O$_y$N$_z$
SiO$_2$ flakes+CaTaO$_2$N
SiO$_2$ flakes+SrTaO$_2$N
SiO$_2$ flakes+Zr$_2$ON$_2$
SiO$_2$ flakes+Zr$_7$O$_8$N$_4$
SiO$_2$ flakes+Ta$_3$N$_5$
SiO$_2$ flakes+TaON
SiO$_2$ flakes+ZrV$_2$O$_4$N$_2$
SiO$_2$ flakes+ZrPr$_6$O$_{10}$N$_2$
SiO$_2$ flakes+TiON+Ta$_3$N$_5$
SiO$_2$ flakes+Ta$_3$N$_5$+TiO$_2$
SiO$_2$ flakes+TiO$_2$+SiO$_2$+Ta$_3$N$_5$
SiO$_2$ flakes+Zr$_2$ON$_2$+TiO$_2$
SiO$_2$ flakes+TiON+Zr$_2$ON$_2$
SiO$_2$ flakes+TiO$_2$+Zr$_2$ON$_2$
Al$_2$O$_3$ flakes+Ta$_x$O$_y$N$_z$
Al$_2$O$_3$ flakes+Zr$_x$O$_y$N$_z$
Al$_2$O$_3$ flakes+V doped Zr$_x$O$_y$N$_z$
Al$_2$O$_3$ flakes+LaTaON$_z$
Al$_2$O$_3$ flakes+Pr doped Zr$_x$O$_y$N$_z$
Al$_2$O$_3$ flakes+CaTaO$_2$N
Al$_2$O$_3$ flakes+SrTaO$_2$N
Al$_2$O$_3$ flakes+Zr$_2$ON$_2$
Al$_2$O$_3$ flakes+Zr$_7$O$_8$N$_4$
Al$_2$O$_3$ flakes+Ta$_3$N$_5$
Al$_2$O$_3$ flakes+TaON
Al$_2$O$_3$ flakes+ZrV$_2$O$_4$N$_2$
Al$_2$O$_3$ flakes+ZrPr$_6$O$_{10}$N$_2$
Al$_2$O$_3$ flakes+TiON+Ta$_3$N$_5$
Al$_2$O$_3$ flakes+Ta$_3$N$_5$+TiO$_2$
Al$_2$O$_3$ flakes+TiO$_2$+SiO$_2$+Ta$_3$N$_5$
Al$_2$O$_3$ flakes+Zr$_2$ON$_2$+TiO$_2$
Al$_2$O$_3$ flakes+TiON+Zr$_2$ON$_2$
Al$_2$O$_3$ flakes+TiO$_2$+Zr$_2$ON$_2$
TiO$_2$ flakes+Ta$_x$O$_y$N$_z$
TiO$_2$ flakes+Zr$_x$O$_y$N$_z$
TiO$_2$ flakes+V doped Zr$_x$O$_y$N$_z$
TiO$_2$ flakes+LaTaON$_z$
TiO$_2$ flakes+Pr doped Zr$_x$O$_y$N$_z$
TiO$_2$ flakes+CaTaO$_2$N
TiO$_2$ flakes+SrTaO$_2$N
TiO$_2$ flakes+Zr$_2$ON$_2$
TiO$_2$ flakes+Zr$_7$O$_8$N$_4$
TiO$_2$ flakes+Ta$_3$N$_5$
TiO$_2$ flakes+TaON
TiO$_2$ flakes+ZrV$_2$O$_4$N$_2$
TiO$_2$ flakes+ZrPr$_6$O$_{10}$N$_2$
TiO$_2$ flakes+TiON+Ta$_3$N$_5$
TiO$_2$ flakes+Ta$_3$N$_5$+TiO$_2$
TiO$_2$ flakes+TiO$_2$+SiO$_2$+Ta$_3$N$_5$
TiO$_2$ flakes+Zr$_2$ON$_2$+TiO$_2$
TiO$_2$ flakes+TiON+Zr$_2$ON$_2$
TiO$_2$ flakes+TiO$_2$+Zr$_2$ON$_2$
Fe$_2$O$_3$ flakes+Ta$_x$O$_y$N$_z$
Fe$_2$O$_3$ flakes+Zr$_x$O$_y$N$_z$
Fe$_2$O$_3$ flakes+V doped Zr$_x$O$_y$N$_z$
Fe$_2$O$_3$ flakes+LaTaON$_z$
Fe$_2$O$_3$ flakes+Pr doped Zr$_x$O$_y$N$_z$
Fe$_2$O$_3$ flakes+CaTaO$_2$N
Fe$_2$O$_3$ flakes+SrTaO$_2$N
Fe$_2$O$_3$ flakes+Zr$_2$ON$_2$
Fe$_2$O$_3$ flakes+Zr$_7$O$_8$N$_4$
Fe$_2$O$_3$ flakes+Ta$_3$N$_5$
Fe$_2$O$_3$ flakes+TaON
Fe$_2$O$_3$ flakes+ZrV$_2$O$_4$N$_2$
Fe$_2$O$_3$ flakes+ZrPr$_6$O$_{10}$N$_2$
Fe$_2$O$_3$ flakes+TiON+Ta$_3$N$_5$
Fe$_2$O$_3$ flakes+Ta$_3$N$_5$+TiO$_2$
Fe$_2$O$_3$ flakes+TiO$_2$+SiO$_2$+Ta$_3$N$_5$
Fe$_2$O$_3$ flakes+Zr$_2$ON$_2$+TiO$_2$
Fe$_2$O$_3$ flakes+TiON+Zr$_2$ON$_2$
Fe$_2$O$_3$ flakes+TiO$_2$+Zr$_2$ON$_2$ BiOCl+Ta$_x$O$_y$N$_z$
BiOCl+Zr$_x$O$_y$N$_z$
BiOCl+V doped Zr$_x$O$_y$N$_z$
BiOCl+LaTaON$_z$
BiOCl+Pr doped Zr$_x$O$_y$N$_z$
BiOCl+CaTaO$_2$N
BiOCl+SrTaO$_2$N
BiOCl+Zr$_2$ON$_2$
BiOCl+Zr$_7$O$_8$N$_4$
BiOCl+Ta$_3$N$_5$
BiOCl+TaON
BiOCl+ZrV$_2$O$_4$N$_2$
BiOCl+ZrPr$_6$O$_{10}$N$_2$
BiOCl+TiON+Ta$_3$N$_5$
BiOCl+Ta$_3$N$_5$+TiO$_2$
BiOCl+TiO$_2$+SiO$_2$+Ta$_3$N$_5$
BiOCl+Zr$_2$ON$_2$+TiO$_2$
BiOCl+TiON+Zr$_2$ON$_2$
BiOCl+TiO$_2$+Zr$_2$ON$_2$
Mica+TiO$_2$+Ta$_x$O$_y$N$_z$
Mica+TiO$_2$+Zr$_x$O$_y$N$_z$
Mica+TiO$_2$+V doped Zr$_x$O$_y$N$_z$
Mica+TiO$_2$+LaTaON$_z$
Mica+TiO$_2$+Pr doped Zr$_x$O$_y$N$_z$
Mica+TiO$_2$+CaTaO$_2$N
Mica+TiO$_2$+SrTaO$_2$N
Mica+TiO$_2$+Zr$_2$ON$_2$
Mica+TiO$_2$+Zr$_7$O$_8$N$_4$
Mica+TiO$_2$+Ta$_3$N$_5$
Mica+TiO$_2$+TaON
Mica+TiO$_2$+ZrV$_2$O$_4$N$_2$
Mica+TiO$_2$+ZrPr$_6$O$_{10}$N$_2$
Mica+TiO$_2$+TiON+Ta$_3$N$_5$
Mica+TiO$_2$+Ta$_3$N$_5$+TiO$_2$
Mica+TiO$_2$+TiO$_2$+SiO$_2$+Ta$_3$N$_5$
Mica+TiO$_2$+Zr$_2$ON$_2$+SiO$_2$+TiO$_2$
Mica+TiO$_2$+TiON+Zr$_2$ON$_2$
Mica+TiO$_2$+TiO$_2$+Zr$_2$ON$_2$
Mica+TiO$_2$+SiO$_2$+TiO$_2$+Ta$_x$O$_y$N$_z$
Mica+TiO$_2$+SiO$_2$+SiO$_2$+TiO$_2$+Zr$_x$O$_y$N$_z$
Mica+TiO$_2$+SiO$_2$+TiO$_2$+V doped Zr$_x$O$_y$N$_z$
Mica+TiO$_2$+SiO$_2$+TiO$_2$+LaTaON$_2$
Mica+TiO$_2$+SiO$_2$+TiO$_2$+Pr doped Zr$_x$O$_y$N$_z$
Mica+TiO$_2$+SiO$_2$+TiO$_2$+CaTaO$_2$N
Mica+TiO$_2$+SiO$_2$+TiO$_2$+SrTaO$_2$N
Mica+TiO$_2$+SiO$_2$+TiO$_2$+Zr$_2$ON$_2$
Mica+TiO$_2$+SiO$_2$+TiO$_2$+Zr$_7$O$_8$N$_4$
Mica+TiO$_2$+SiO$_2$+TiO$_2$+Ta$_3$N$_5$
Mica+TiO$_2$+SiO$_2$+TiO$_2$+TaON
Mica+TiO$_2$+SiO$_2$+TiO$_2$+ZrV$_2$O$_4$N$_2$
Mica+TiO$_2$+SiO$_2$+TiO$_2$+ZrPr$_6$O$_{10}$N$_2$
Mica+TiO$_2$+SiO$_2$+TiO$_2$+TiON+Ta$_3$N$_5$
Mica+TiO$_2$+SiO$_2$+TiO$_2$+Ta$_3$N$_5$+TiO$_2$
Mica+TiO$_2$+SiO$_2$+TiO$_2$+TiO$_2$+SiO$_2$+Ta$_3$N$_5$
Mica+TiO$_2$+SiO$_2$+TiO$_2$+Zr$_2$ON$_2$+TiO$_2$
Mica+TiO$_2$+SiO$_2$+TiO$_2$+TiON+Zr$_2$ON$_2$
Mica+TiO$_2$+SiO$_2$+TiO$_2$+TiO$_2$+Zr$_2$ON$_2$ The interference color is determined by the optical thickness, which is the geometrical thickness of the layer multiplied by the refractive index (Pfaff, G.; Reynders, P. "Angle-dependent optical effects deriving from submicron structures of films and pigments", Chemical Reviews, 99 (1999), p. 1963–1981). The latter is a strong function of the chosen nitride respectively oxynitride but is in general not known for the rather new materials mentioned in this invention. The mass tone of the absorbing pigments is as well a function of the layer thickness. Therefore, the desired color effect is empirically optimized by adjustment of the amount of precursor, leading to a precursor layer thickness, and consequent reaction with the reactive gases.

The nitride respectively oxynitride layer can be coated directly onto the substrate, platelet-shaped, spherical or acicular substrates, as described above. Nitride respectively oxynitride layer coated particles can be used as substrates to precipitate the low refractive or high refractive optical layers, such as silicon dioxide, aluminum oxide, titanium oxides, iron oxides, ilmenite or pseudobrookite. The deposition of thin semi-transparent metal layers, such as chromium, silver, copper and aluminum, onto the nitride respectively oxynitride layers is also possible.

The mean diameter of the substrates and hence the resulting pigments can vary between 1 and 500 μm, preferably between 5 and 50 μm. For the flaky substrates and pronounced interference effects the preferred mean diameter is chosen between 5 and 150 μm. Such substrates are commercially available or can be obtained by known processes.

The advantage of this invention is the combination of a great variety of different mass-tones of various nitrides and oxynitrides with an angle dependent interference color that is adjusted by the layer thickness of the nitride, respectively oxynitride layer.

To enhance the light and weather stability it is frequently advisable depending on the field of application, to subject the inventive pearlescent pigments to a surface treatment. Useful surface treatments and aftertreatments include for example the processes described in DE C 22 15 191, DE-A 31 51 354, DE-A 32 35 017 or DE-A 33 34 598, DE 40 30 727 A1, EP 0 649 886 A2, WO 97/29059, WO 99/57204, U.S. Pat. No. 5,729,255. This surface treatment further enhances the chemical stability of the pigments and/or facilitates the handling of the pigments, especially its incorporation into various application media.

The pearlescent pigments of the present invention are advantageously useful for many purposes, such as the coloring of plastics, glasses, ceramic products, agricultural foils, decorative cosmetic formulations, and in particular coatings, powder coatings, especially automotive coatings, and inks, including printing inks. All customary printing processes can be employed, for example offset printing, intaglio printing, bronzing, flexographic printing. Additionally the inventive pigments are suitable for the lasermarking of papers and plastics, for security applications like for example banknotes, ID cards, credit cards, concert tickets and plastic films.

The pearlescent pigments of the present invention are also advantageously useful for these purposes in admixture with filler pigments or transparent and hiding white, colored and black organic and inorganic pigments and also with conventional transparent, colored and black luster pigments based on metal oxide coated mica, TiO$_2$ flakes, SiO$_2$ flakes or Al$_2$O$_3$ flakes and coated or uncoated metal pigments, BiOCl pigments, platelet shaped iron oxides, or graphite flakes. The inventive pigments can be further coated with organic or inorganic layers to yield combination pigments.

The examples which follow are intended to illustrate the invention without, however, limiting it.

The entire disclosures of all applications, patents and publications, cited herein and of corresponding European application No. 02002448.5, filed Feb. 1, 2002, are incorporated by reference herein.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

Example 1

100 g of mica muscovite (diameter 10–50 $\mu$m) of Merck KGaA, Darmstadt, Germany are suspended in 2 liters of fully deionized water. The suspension is heated to 75° C. A $TaCl_5$-solution (81 g $TaCl_5$ diluted with 200 g HCl) is slowly added in the reactor. The pH of the solution is kept at pH 9 by addition of dilute hydrochloric acid solution. The preparation is filtered off, washed with completely deionized water, dried at 110° C. for 12 hours. As a result, 5 g of $Ta_2O_5$ are precipitated onto 100 g of mica. This precursor material is then put into a fluidized bed reactor, calcined under ammonia at 1000° C. during 48 hours. A red $Ta_3N_5$ coated mica pigment is obtained.

Example 2

100 g Iriodin® 100 ($TiO_2$ coated/mica pigment of Merck KGaA, Darmstadt, Germany) are suspended in 2 liters of fully deionized water. The suspension is heated to 75° C. A $ZrOCl_2$ solution (72.3 g diluted in 600 ml water) is slowly added in the reactor. The pH of the solution is kept at pH 3 by addition of 15% aqueous sodium hydroxide solution. The preparation is filtered off, washed with completely deionized water and dried at 110° C. for 12 hours. As result, 50 g of $ZrO_2$ are precipitated onto 100 g of Iriodin® 100. This precursor material is then put into a fluidized bed reactor. The precursor is fluidized with $N_2$ to 750–850° C. and then is reacted with $NH_3$ for 360 minutes. A pigment with a blue color (titanium oxynitride) and a yellow shade (zirconium oxynitride) is obtained.

Example 3

100 g Iriodin® 100 are suspended in 2 liters of fully deionized water. The suspension is heated to 75° C. A $TaCl_5$ solution (81 g $TaCl_5$ diluted with 200 g HCl) is slowly added in the reactor. The pH of the solution is kept at pH 9 by addition of dilute hydrochloric acid solution. The preparation is filtered off, washed with completely deionized water, dried at 110° C. for 12 hours and then calcined at 750° C. for 30 minutes. As result, 50 g of $Ta_2O_5$ are precipitated onto 100 g of mica. This precursor material is then put into a fluidized bed reactor, calcined under ammonia at 850° C. during 60 to 360 minutes. A red tantalum oxynitride is obtained.

Example 4

100 g $SiO_2$ flakes (diameter 10–50 $\mu$m) of Merck KGaA, Darmstadt, Germany are suspended in 2 liters of fully deionized water. The suspension is heated to 75° C. A $ZrOCl_2$ solution (72.3 g diluted in 600 ml water) is slowly added in the reactor. The pH of the solution is kept at pH 3 by addition of 15% aqueous sodium hydroxide solution. The preparation is filtered off, washed with completely deionized water, dried at 110° C. for 12 hours. As result, 50 g of $ZrO_2$ are precipitated onto 100 g of $SiO_2$ flakes. The dried precursor material is then put into the fluidized bed, calcined at 1100° C. under $NH_3$ for 24 hours and then slowly cooled to 900° C. and calcined at 900° C. for 24 hours. A yellow pigment of zirconium oxynitride coated $SiO_2$-flakes, is obtained.

Example 5

50 g of $ZrO_2$: $VCl_3$(10:1 wt.-ratio) are precipitated onto 100 g of $SiO_2$-flakes using a $ZrOCl_2$-solution (72,3 g of $ZrOCl_2$-solution containing 7,2 g of $VCl_3$ diluted into 600 ml of water) as described in example 4. The dried precursor material is then put into the fluidized bed, calcined at 1100° C. under $NH_3$ for 24 hours and then slowly cooled to 900° C. and calcined at 900° C. for 24 hours. A pigment with a blue color, vanadium-doped zirconium oxynitride is obtained.

Example 6

42 g $La(NO_3)_3$ and 36 g $Ta(NO_3)_3$ solutions were mixed with 12 g oxalic acid. The solution is slowly added to a mica muscovite suspension (diameter<15 $\mu$m) of Merck KGaA, Darmstadt, Germany. As a result, $LaTaO_4$ is precipitated onto mica and then the pigment is dried at 110° C. for 12 hours. The dried precursor material is put into a fluidized bed, calcined at 850° C. under $NH_3$ for 30 to 360 hours. A red pigment of mixed lanthanum tantalum oxynitride phases is obtained.

Example 7

A metallized zirconium oxynitride pigment is produced by thermally decomposing chromium hexacarbonyl in the presence of heated zirconium oxynitride coated onto $SiO_2$ flakes as described in the example 4. This pigment is fluidized with nitrogen to achieve and maintain a non-bubbling fluidized bed and an oxygen free atmosphere. Then the reactor is heated to 400–450° C. and kept on this steady condition throughout the following coating process. A stream of nitrogen loaded with chromium hexacarbonyl is prepared by passing nitrogen through a flask containing chromium hexacarbonyl, which is kept at 80° C., and introduced subsequently into the reactor. The vaporized compound is passed into the tube for about 1.5 hours. About 5 nm of chromium is deposited on the zirconium oxynitride pigment based onto $SiO_2$ flakes, forming a semitransparent layer. The organic by-product of the decomposition reaction passed out of the tube into a scrubber.

Example 8

100 g of $SiO_2$ flakes (Merck KGaA, Darmstadt, Germany, diameter 10–50 $\mu$m) are suspended in 2 liters of fully deionized water. The suspension is heated to 75° C. Then, a solution of 81 g $TaCl_5$ diluted with 200 g ethanol is slowly added into the reactor. The pH of the solution is kept at pH 2 by addition of aqueous 15 wt.-% NaOH solution. The preparation is filtered off, washed with completely deionized water, and dried at 110° C. for 12 hours. As a result, 50 g of $Ta_2O_5$ were precipitated onto 100 g of $SiO_2$ flakes. This precursor is then calcined under ammonia at 900° C. for 12 hours in a fluidized bed reactor. An effect pigment is obtained having a bright orange mass tone and a blue interference color. The resulting pigment becomes more reddish if oxygen is carefully excluded from the reaction.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A pearlescent pigment comprising a substrate and one or more layers wherein at least one layer is selectively light absorbing and comprises a nitride and/or oxynitride with the proviso that the pigment does not contain a layer of titanium nitride or titanium oxynitride.

2. A pearlescent pigment according to claim 1, wherein the substrate is platelet-shaped, spherical or acicular.

3. A pearlescent pigment according to claim 2, wherein the substrate is micaceous iron oxide, mica, basic lead carbonate, flaky barium sulfate, $SiO_2$, $Al_2O_3$, $TiO_2$, glass, ZnO, $ZrO_2$, $SnO_2$, BiOCl, chromium oxide, BN, MgO flakes, $Si_3N_4$, graphite, a pearlescent pigment, a pearlescent multilayer pigment, or coated or uncoated $SiO_2$ sphere.

4. A pearlescent pigment according to claim 1, wherein the nitride and/or oxynitride is a binary nitride, a ternary nitride or an oxynitride based on two or three metals.

5. A process for the preparation of a pearlescent pigment according to claim 1, which comprises precipitating a layer of one or more metal oxides onto a substrate and then converting the layer into a nitride and or oxynitride.

6. A process according to claim 5, wherein the one or more metal oxide is doped with metal ions, phosphate ions and/or sulfate ions.

7. A process according to claim 5, wherein the conversion is carried out in a fluidized bed reactor.

8. A pigment composition comprising a pigment of claim 1 and a plastic, glass, ceramic, powder coating, paint, ink, agricultural foil, paper or cosmetic.

9. The process of claim 5, wherein the converting into a nitride or oxynitride is effected by reaction with a nitrogen-containing reaction gas at a temperature of 700 to 1250° C.

10. The process of claim 9, wherein the reaction gas is ammonia, $N_2$ or a $N_2/H_2$ mixture.

11. The process of claim 9, wherein the reaction temperature is 800 to 1100° C.

12. The process of claim 9, wherein the reaction gas is ammonia.

13. The pigment of claim 1, wherein at least one selectively light absorbing layer comprising a nitride and/or oxynitride has a thickness of from 5 to 500 nm.

14. The pigment of claim 1, wherein at least one light absorbing layer comprising a nitride and/or oxynitride has a thickness of from 50 to 350 nm.

15. The pigment of claim 1, which is a pigment having one of the following combinations of substrate and layer(s):

Mica+$Ta_xO_yN_z$,
Mica+$Zr_xO_yN_z$,
Mica+V doped $Zr_xO_yN_z$,
Mica+$LaTaON_2$,
Mica+Pr doped $Zr_xO_yN_z$,
Mica+$CaTaO_2N$,
Mica+$SrTaO_2N$,
Mica+$Zr_2ON_2$,
Mica+$Zr_7O_8N_4$,
Mica+$Ta_3N_5$,
Mica+TaON,
Mica+$ZrV_2O_4N_2$,
Mica+$ZrPrO_{10}N_2$,
Mica+$Ta_3N_5$+$TiO_2$,
Mica+$TiO_2$+$SiO_2$+$Ta_3N_5$,
Mica+$Zr_2ON_2$+$TiO_2$,
Mica+$TiO_2$+$Zr_2ON_2$,
$SiO_2$ flakes+$Ta_xO_yN_z$,
$SiO_2$ flakes+$Zr_xO_yN_z$,
$SiO_2$ flakes+V doped $Zr_xO_yN_z$,
$SiO_2$ flakes+$LaTaON_2$,
$SiO_2$ flakes+Pr doped $Zr_xO_yN_z$,
$SiO_2$ flakes+$CaTaO_2N$,
$SiO_2$ flakes+$SrTaO_2N$,
$SiO_2$ flakes+$Zr_2ON_2$,
$SiO_2$ flakes+$Zr_7O_8N_4$,
$SiO_2$ flakes+$Ta_3N_5$,
$SiO_2$ flakes+TaON,
$SiO_2$ flakes+$ZrV_2O_4N_2$,
$SiO_2$ flakes+$ZrPr_6O_{10}N_2$,
$SiO_2$ flakes+$Ta_3N_5$+$TiO_2$,
$SiO_2$ flakes+$TiO_2$+$SiO_2$+$Ta_3N_5$,
$SiO_2$ flakes+$Zr_2ON_2$+$TiO_2$,
$SiO_2$ flakes+$TiO_2$+$Zr_2ON_2$,
$Al_2O_3$ flakes+$Ta_xO_yN_z$,
$Al_2O_3$ flakes+$Zr_xO_yN_z$,
$Al_2O_3$ flakes+V doped $Zr_xO_yN_z$,
$Al_2O_3$ flakes+$LaTaON_2$,
$Al_2O_3$ flakes+Pr doped $Zr_xO_yN_z$,
$Al_2O_3$ flakes+$CaTaO_2N$,
$Al_2O_3$ flakes+$SrTaO_2N$,
$Al_2O_3$ flakes+$Zr_2ON_2$,
$Al_2O_3$ flakes+$Zr_7O_8N_4$,
$Al_2O_3$ flakes+$Ta_3N_5$,
$Al_2O_3$ flakes+TaON,
$Al_2O_3$ flakes+$ZrV_2O_4N_2$,
$Al_2O_3$ flakes+$ZrPr_6O_{10}N_2$,
$Al_2O_3$ flakes+$Ta_3N_5$+$TiO_2$,
$Al_2O_3$ flakes+$TiO_2$+$SiO_2$+$Ta_3N_5$,
$Al_2O_3$ flakes+$Zr_2ON_2$+$TiO_2$,
$Al_2O_3$ flakes+$TiO_2$+$Zr_2ON_2$,
$TiO_2$ flakes+$Ta_xO_yN_z$,
$TiO_2$ flakes+$Zr_xO_yN_z$,
$TiO_2$ flakes+V doped $Zr_xO_yN_z$,
$TiO_2$ flakes+$LaTaON_2$,
$TiO_2$ flakes+Pr doped $Zr_xO_yN_z$,
$TiO_2$ flakes+$CaTaO_2N$,
$TiO_2$ flakes+$SrTaO_2N$,
$TiO_2$ flakes+$Zr_2ON_2$,
$TiO_2$ flakes+$Zr_7O_8N_4$, $TiO_2$ flakes+$Ta_3N_5$,
$TiO_2$ flakes+TaON,
$TiO_2$ flakes+$ZrV_2O_4N_2$,
$TiO_2$ flakes+$ZrPr_6O_{10}N_2$,
$TiO_2$ flakes+$Ta_3N_5$+$TiO_2$,
$TiO_2$ flakes+$TiO_2$+$SiO_2$+$Ta_3N_5$,
$TiO_2$ flakes+$Zr_2ON_2$+$TiO_2$,
$TiO_2$ flakes+$TiO_2$+$Zr_2ON_2$,
$Fe_2O_3$ flakes+$Ta_xO_yN_z$,
$Fe_2O_3$ flakes+$Zr_xO_yN_z$,
$Fe_2O_3$ flakes+V doped $Zr_xO_yN_z$,
$Fe_2O_3$ flakes+$LaTaON_2$,
$Fe_2O_3$ flakes+Pr doped $Zr_xO_yN_z$,
$Fe_2O_3$ flakes+$CaTaO_2N$,
$Fe_2O_3$ flakes+$SrTaO_2N$,
$Fe_2O_3$ flakes+$Zr_2ON_2$,
$Fe_2O_3$ flakes+$Zr_7O_8N_4$,
$Fe_2O_3$ flakes+$Ta_3N_5$,
$Fe_2O_3$ flakes+TaON,
$Fe_2O_3$ flakes+$ZrV_2O_4N_2$,
$Fe_2O_3$ flakes+$ZrPr_6O_{10}N_2$,
$Fe_2O_3$ flakes+$Ta_3N_5$+$TiO_2$,
$Fe_2O_3$ flakes+$TiO_2$+$SiO_2$+$Ta_3N_5$,
$Fe_2O_3$ flakes+$Zr_2ON_2$+$TiO_2$,
$Fe_2O_3$ flakes+$TiO_2$+$Zr_2ON_2$,
BiOCl+$Ta_xO_yN_z$,
BiOCl+$Zr_xO_yN_z$,
BiOCl+V doped $Zr_xO_yN_z$,
BiOCl+$LaTaON_2$,
BiOCl+Pr doped $Zr_xO_yN_z$,
BiOCl+$CaTaO_2N$,
BiOCl+$SrTaO_2N$,
BiOCl+$Zr_2ON_2$,
BiOCl+$Zr_7O_8N_4$,
BiOCl+$Ta_3N_5$,
BiOCl+TaON,
BiOCl+$ZrV_2O_4N_2$,
BiOCl+$ZrPr_6O_{10}N_2$,
BiOCl+$Ta_3N_5$+$TiO_2$,
BiOCl+$TiO_2$+$SiO_2$+$Ta_3N_5$,
BiOCl+$Zr_2ON_2$+$TiO_2$,
BiOCl+$TiO_2$+$Zr_2ON_2$,
Mica+$TiO_2$+$Ta_xO_yN_z$,
Mica+$TiO_2$+$Zr_xO_yN_z$,
Mica+$TiO_2$+V doped $Zr_xO_yN_z$,
Mica+$TiO_2$+$LaTaON_2$,
Mica+$TiO_2$+Pr doped $Zr_xO_yN_z$,
Mica+$TiO_2$+$CaTaO_2N$,
Mica+$TiO_2$+$SrTaO_2N$,
Mica+$TiO_2$+$Zr_2ON_2$,
Mica+$TiO_2$+$Zr_7O_8N_4$,
Mica+$TiO_2$+$Ta_3N_5$,
Mica+$TiO_2$+TaON,
Mica+$TiO_2$+$ZrV_2O_4N_2$,
Mica+$TiO_2$+$ZrPr_6O_{10}N_2$,
Mica+$TiO_2$+$Ta_3N_5$+$TiO_2$,
Mica+$TiO_2$+$TiO_2$+$SiO_2$+$Ta_3N_5$,
Mica+$TiO_2$+$Zr_2ON_2$+$TiO_2$,
Mica+$TiO_2$+$TiO_2$+$Zr_2ON_2$,
Mica+$TiO_2$+$SiO_2$+$TiO_2$+$Ta_xO_yN_z$,
Mica+$TiO_2$+$SiO_2$+$TiO_2$+$Zr_xO_yN_z$,
Mica+$TiO_2$+$SiO_2$+$TiO_2$+V doped $Zr_xO_yN_z$,
Mica+$TiO_2$+$SiO_2$+$TiO_2$+$LaTaON_2$,
Mica+$TiO_2$+$SiO_2$+$TiO_2$+Pr doped $Zr_xO_yN_z$,
Mica+$TiO_2$+$SiO_2$+$TiO_2$+$CaTaO_2N$,
Mica+$TiO_2$+$SiO_2$+$TiO_2$+$SrTaO_2N$,
Mica+$TiO_2$+$SiO_2$+$TiO_2$+$Zr_2ON_2$,
Mica+$TiO_2$+$SiO_2$+$TiO_2$+$Zr_7O_8N_4$,
Mica+$TiO_2$+$SiO_2$+$TiO_2$+$Ta_3N_5$,
Mica+$TiO_2$+$SiO_2$+$TiO_2$+TaON,
Mica+$TiO_2$+$SiO_2$+$TiO_2$+$ZrV_2O_4N_2$,
Mica+$TiO_2$+$SiO_2$+$TiO_2$+$ZrPr_6O_{10}N_2$,
Mica+$TiO_2$+$SiO_2$+$TiO_2$+$Ta_3N_5$+$TiO_2$,
Mica+$TiO_2$+$SiO_2$+$TiO_2$+$TiO_2$+$SiO_2$+$Ta_3N_5$,
Mica+$TiO_2$+$SiO_2$+$TiO_2$+$Zr_2ON_2$+$TiO_2$,
Mica+$TiO_2$+$SiO_2$+$TiO_2$+$TiO_2$+$Zr_2ON_2$.

16. A pigment composition of claim 8, wherein the composition is in the form of a coating composition.

17. A pigment composition of claim 8, wherein the composition is in the form of a printing ink composition.

18. A pigment composition of claim 8, wherein the composition is in the form of a laser-markable paper or plastic.

19. A pigment composition of claim 8, wherein the composition is in the form of a security application.

* * * * *